US008814818B2

(12) United States Patent
Bushby (10) Patent No.: US 8,814,818 B2
(45) Date of Patent: *Aug. 26, 2014

(54) DISPOSABLE TWO-PART ORTHOTIC FOOT SUPPORT STRAP SYSTEM AND METHOD

(75) Inventor: Donald P. Bushby, Houston, TX (US)

(73) Assignee: Applied BioKinetics LLC, Houston, TX (US)

(*) Notice: Subject to any disclaimer, the term of this patent is extended or adjusted under 35 U.S.C. 154(b) by 316 days.

This patent is subject to a terminal disclaimer.

(21) Appl. No.: 13/365,237

(22) Filed: Feb. 2, 2012

(65) Prior Publication Data

US 2014/0107552 A1    Apr. 17, 2014

Related U.S. Application Data

(63) Continuation-in-part of application No. 12/876,060, filed on Sep. 3, 2010, now abandoned, which is a continuation-in-part of application No. 11/165,304, filed on Jun. 23, 2005, now Pat. No. 8,216,162, which is a continuation-in-part of application No. 10/817,172, filed on Apr. 2, 2004, now Pat. No. 8,414,511.

(51) Int. Cl.
*A61F 5/00* (2006.01)
*A61F 13/06* (2006.01)
*B29D 11/00* (2006.01)
*A43B 13/34* (2006.01)

(52) U.S. Cl.
USPC ............... 602/28; 36/35 R; 523/108; 602/61

(58) Field of Classification Search
CPC ........................................ A61F 5/01

USPC ......... 602/1, 28, 29; 36/140, 43, 44; 706/924, 706/932, 934; 704/270; 206/363, 438, 440, 206/441, 828; 423/108–118
See application file for complete search history.

(56) References Cited

U.S. PATENT DOCUMENTS 1,351,248 A    8/1920    Hill
1,492,514 A    4/1924    Harris
(Continued)

FOREIGN PATENT DOCUMENTS

EP    0621023 A2    10/1994
WO    80/01758 B2    9/1980
(Continued)

OTHER PUBLICATIONS

Schulthies et al.; A Modified Low-Dye Taping Technique to Support the Medial Longitudinal Arch and Reduce Excessive Pronation; J Antl Train; 30(3):266-268; Sep. 1995.

(Continued)

*Primary Examiner* — Patricia Bianco
*Assistant Examiner* — Tarla Patel
(74) *Attorney, Agent, or Firm* — Shay Glenn LLP (57) ABSTRACT

An ultrathin sole strap with a pair of heel tabs and an ultrathin arch strap formed of flexible, non-resilient non-stretch woven microfiber material having an adhesive layer on an underside surface for adhesive application to a foot individually or in combination. The sole strap is adhered along the ball, the midfoot, and the heel of the foot, and the heel tabs are adhered to the back side of the heel in crossed relation. The sole strap functions as a tensile load bearing member in the region between the ball and the heel of the foot during the heel contact phase, weight bearing midstance phase, and propulsion phases of a walking gait cycle, to bear major tensile loads and stresses which would otherwise be absorbed primarily by the plantar fascia. The arch strap adhered transversely over the sole support strap and arch of the foot provides additional support and stability.

20 Claims, 6 Drawing Sheets

(56) References Cited

U.S. PATENT DOCUMENTS

| | | | |
|---|---|---|---|
| 1,566,063 | A | 12/1925 | Barry |
| 1,577,203 | A | 3/1926 | Cramer |
| 1,717,609 | A | 6/1929 | Ludwig |
| 1,980,621 | A | 11/1934 | Innis |
| 2,182,843 | A | 12/1939 | Flynn et al. |
| 2,410,078 | A | 10/1946 | Waldo |
| 2,454,836 | A | 11/1948 | Rayner |
| 2,572,152 | A | 10/1951 | Horlacher |
| 2,633,130 | A | 3/1953 | Scholl |
| 2,985,970 | A | 5/1961 | McCarthy |
| 3,327,410 | A | 6/1967 | Park et al. |
| 3,449,844 | A | 6/1969 | Spence |
| 3,482,683 | A | 12/1969 | Desnoyers |
| 3,508,544 | A | 4/1970 | Moore et al. |
| 3,584,622 | A | 6/1971 | Domenico |
| 4,271,605 | A | 6/1981 | Raczka |
| 4,392,487 | A | 7/1983 | Selmer et al. |
| 4,510,699 | A | 4/1985 | Nakamura et al. |
| 4,702,948 | A | 10/1987 | Sieber-Gadient |
| 4,751,784 | A | 6/1988 | Petker et al. |
| 4,753,228 | A | 6/1988 | Selmer et al. |
| 4,860,464 | A | 8/1989 | Misevich et al. |
| 4,997,709 | A | 3/1991 | Huddleston |
| 5,473,781 | A | 12/1995 | Greenberg |
| 5,559,165 | A | 9/1996 | Paul |
| 5,840,053 | A | 11/1998 | Roth |
| 5,861,348 | A | 1/1999 | Kase |
| 5,865,779 | A | 2/1999 | Gleason |
| 5,897,518 | A | 4/1999 | Shaw |
| 6,120,473 | A | 9/2000 | Oliverio |
| 6,436,020 | B1 | 8/2002 | Weingand |
| 6,640,465 | B1 | 11/2003 | Burgess |
| 6,641,550 | B1 | 11/2003 | Johnson |
| 6,684,442 | B1 | 2/2004 | Parker et al. |
| 6,775,929 | B2 | 8/2004 | Katz et al. |
| 7,902,420 | B2 | 3/2011 | Kase |
| 8,216,162 | B2 | 7/2012 | Bushby |
| 8,414,511 | B2 | 4/2013 | Bushby |
| 2002/0188239 | A1 | 12/2002 | Turtzo |
| 2003/0145495 | A1 | 8/2003 | Green |
| 2003/0212358 | A1 | 11/2003 | Cavanagh et al. |
| 2004/0006814 | A1 | 1/2004 | Holden |
| 2004/0118017 | A1 | 6/2004 | Dalton et al. |
| 2004/0261294 | A1 | 12/2004 | Kawata |
| 2005/0011084 | A1 | 1/2005 | Stephenson |
| 2005/0251073 | A1 | 11/2005 | Roth |
| 2007/0283597 | A1 | 12/2007 | Logan |
| 2012/0232452 | A1 | 9/2012 | Bushby |

FOREIGN PATENT DOCUMENTS

| | | |
|---|---|---|
| WO | 02/43517 A1 | 6/2002 |
| WO | 02/43518 A2 | 6/2002 |
| WO | 02/43519 A1 | 6/2002 |

OTHER PUBLICATIONS

Dreamy Feet Co.; Adhesive Paddings (product info.); 9 pgs.; downloaded Aug. 3, 2005 from the internet: (http://www.dreamyfeet.co.uk/adhesive_padding.htm).

My Foot Shop; Plantar Fasciitis (information); © 2001; 10 pgs.; downloaded Sep. 11, 2008 from the internet: (http//web.archive.org/web/20030709195412/myfootshop.com/detail.asp?Condition=Plant).

Sports Injury Clinic; Taping for Plantar Fasciitis (instructions); 2 pgs.; downloaded Mar. 10, 2004 from the internet: (http:www.sportsinjuryclinic.net/cybertherapis/front/foot/plantarfasciitis/plantartaping.php).

ACE; Coach's Taping Kit (product image); 1 pg.; downloaded May 8, 2005 from the internet: (http://tsa.imageg.net/graphics/productimages/pG01-1049858dt.jpg).

The Sports Authority; Ace Coach's Taping Kit (product info.); 2 pgs.; downloaded May 10, 2005 from the internet: (http://www.thesportsauthority.com/smi-ace-coach-taping-kit-pi-134240).

Dr. Scholl's; Moleskin Plus Padding (product page); 1 pg.; downloaded May 10, 2005 from the Internet: (http://www.drscholls.com/product.aspx?prodid=5).

KBA Coach; Spenco Adhesive Knit (product info.); 1 pg.; downloaded May 10, 2005 from the internet: (http://www.kbacoach.com/spenadkit).

Kinesio Taping; taping instructions; 2 pgs.; downloaded May 10, 2005 from the internet: (http://kinesiotaping.com/content.asp?CustComKey=96149&CategoryKey=31687&pn=Pag).

Jaybird & Mais; Adhesive Tape (product info.); 4 pgs.; downloaded May 10, 2005 from the internet: (http://www.jaybird.co/RigidTape.asp).

Wisdomking.Com; Leukotape P Sports Tape (product info.); 1 pg.; downloaded May 10, 2005 from the internet (http://www.wisdomking.com/product12127.html).

Fieldtex; Ankle Taping (product info. & taping procedure); 2 pgs.; downloaded from the Internet: www.fieldtex.com; (this web address was available to applicant(s) at least as of Jun. 23, 2005).

Readykor; Basic Sports Taping Kit (product info.); 1 pg.; downloaded from the internet May 8, 2005 from (http//www.readykor.com/sport/BP-697.html).

Grisogono; Running Fitness and Injuries. A Self-Help Guide; New Zealand Ed.; Reed Publishing, Auckland, NZ; pp. 126-127; (year of pub. sufficiently earlier than effective US filed and any foreign priority date) 1995.

Austin et al.; Illustrated Guide to Taping Techniques; A Moseby Ltd.; Oxford GB; pp. 58-71; (year of pub. sufficiently earlier than effective US filed and any foreign priority date) 1994.

Vonhof; Fixing Your Feet: Prevention and Treatments for Athletes; 4th Ed.; Wilderness Press; Birmingham AL; pp. 270-278; Jul. 2006.

Applied Biokinetics LLC; FasciaDerm® Product Information; printed from website (http://www.fasciaderm.com); 4 pgs.; printed Nov. 7, 2013.

Larue; Adhesive Strapping in Sports for Foot (Videotape); Publisher: Roland E. LaRue, Lincoln, NE; 33 min.; (year of pub. sufficiently earlier than effective US filed and any foreign priority date) 1998.

Bushby; U.S. Appl. No. 13/602,150 entitled "Disposable Two-Part Orthotic Foot Support Strap System and Method," filed Sep. 1, 2012.

Bushby; U.S. Appl. No. 14/477,015 entitled "System for Treatment of Plantar Fasciiis," filed May 21, 2012.

Bushby; U.S. Appl. No. 12/876,060 entitled "Disposable Orthotic Foot Support System," filed Sep. 3, 2010.

DISPOSABLE TWO-PART ORTHOTIC FOOT SUPPORT STRAP SYSTEM AND METHOD

CROSS REFERENCE TO RELATED APPLICATIONS

This application is a Continuation-In-Part of, and claims priority of, U.S. patent application Ser. No. 12/876,060, filed on Sep. 3, 2010, now abandoned, which is a Continuation-In-Part of, and claims priority of, U.S. patent application Ser. No. 11/165,304, filed on Jun. 23, 2005, now U.S. Pat. No. 8,216,162, which is a Continuation-In-Part of, and claims priority of, U.S. patent application Ser. No. 10/817,172, filed on Apr. 2, 2004, now U.S. Pat. No. 8,414,511.

BACKGROUND OF THE INVENTION

1. Field of the Invention

This invention relates generally to orthopedic devices for the foot and, more particularly, to a disposable two-part non-resilient, non-stretch orthotic foot support strap system having a sole support strap member and an arch support strap member that can be adhesively applied to a foot individually or together for reducing tensile loads and stresses and providing anatomical support and stability to the musculoskeletal system and the sole, arch and heel of a foot of a user, and relief from plantar fasciitis.

2. Background Art

Many people suffer from excessive foot strain and conditions such as plantar fasciitis. Plantar fasciitis often occurs in individuals who undergo long periods of weight bearing or undergo sudden changes of weight bearing. Other factors that may lead to this condition include obesity, weight gain, jobs that require a lot of walking on hard surfaces, shoes with little or no arch support. A description of the foot structure leading to this condition is provided as background for understanding the present invention.

Figure 1:
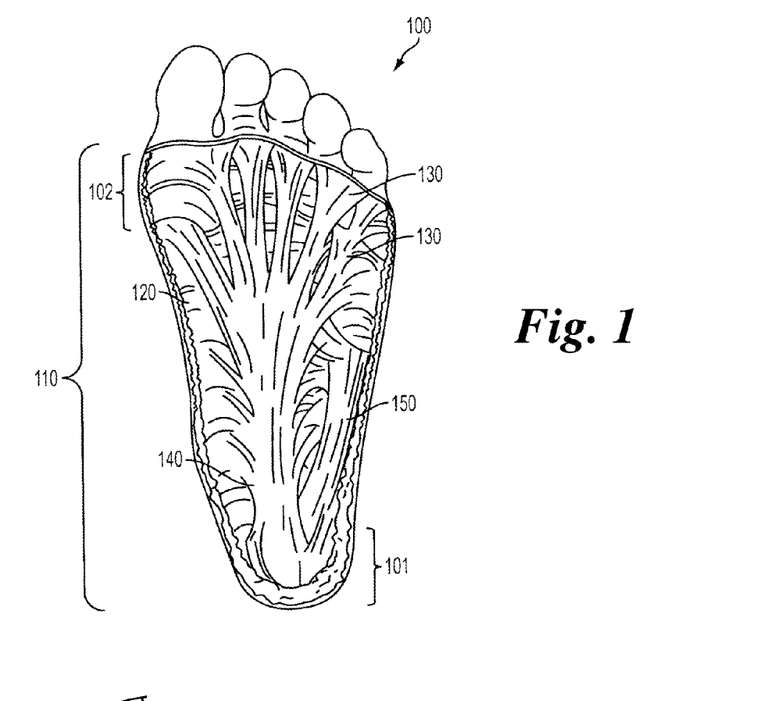
FIG. 1 is an illustration showing parts of a plantar fascia in a dissected bottom view of a human foot.

A dissected bottom view of a human foot 100 is shown in FIG. 1 to illustrate some of the parts of a plantar fascia 110 located in the bottom of the human foot 100. The plantar fascia 110 extends from about the location of the heel 101 to about the location of the ball 102 of the foot. The plantar fascia 110 includes medial plantar fascia 120, superficial tracts 130, a central component of the plantar fascia 140, and a lateral component of the plantar fascia 150. The separate portions of the plantar fascia 110 act as a shock absorber while walking and transfer tensile forces along the bottom of the foot 100.

Figure 2:
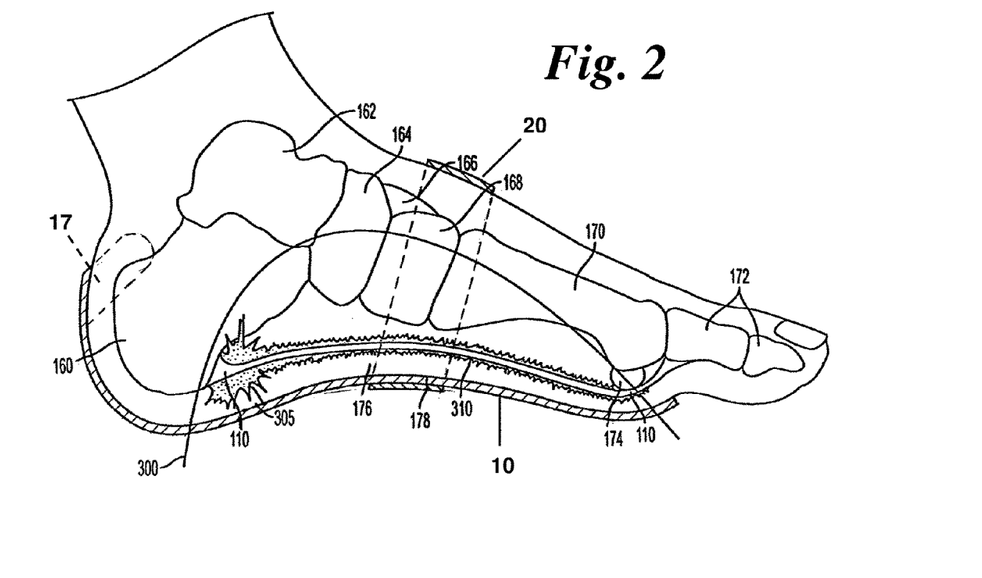
FIG. 2 is a cross sectional side view showing the tissue and bone structure in the human foot.

A cross sectional side view of tissue and bone structure in the human foot 100 is shown in FIG. 2. The human foot 100 includes the plantar fascia 110, a plantar calcaneus 160, a talus 162, a navicular 164, a cuneiform 166, a cuboid 168, metatarsals 170, phalanges 172, a sesamoid 174, a fat pad area 176, and an outer skin surface 178. As seen from the side, the plantar calcaneus 160, the talus 162, the navicular 164, the cuneiform 166, the cuboid 168, the metatarsals 170, and the sesamoid 174 form what resembles the shape of an arch. This shape is commonly referred to as the longitudinal arch. Another arch commonly referred to as the transverse arch (metatarsal) also exists in about the same area in a perpendicular direction that runs laterally across the width of the foot.

The plantar fascia 110 provides anatomical support to the foot as it serves the vital role of maintaining the shape of the two anatomical arches of the foot, the transverse arch and the longitudinal arch. As illustrated in FIGS. 1 and 2, the plantar fascia 110 runs across the bottom of the foot 100 from the heel 101 to the ball 102 and spreads out across the width of the foot 100. As longitudinal and lateral tensile stresses are produced in the bottom of the foot 100, the plantar fascia 110 absorbs the tensile forces and maintains the shape of the two anatomical arches.

For example, while standing or while in motion, forces experienced by the foot 100 act in a direction which tends to flatten the arches. The stress line 300 in FIG. 2 shows an approximation of the line of forces transferred through foot 100 during typical motion. As shown in FIG. 2, the stress line 300 resembles the shape of an archer's bow. The plantar fascia 110 running along near the bottom surface of the foot 100 is analogous to a string in the archer's bow. Forces that tend to move the ends of the bow apart increase tension on the string. FIG. 2 also shows a sole support strap member 10 and an arch support strap member 20 of the present two-part non-resilient, non-stretch orthotic foot support strap system, illustrated somewhat schematically and with a greater thickness for visibility, attached to the sole of the foot, and will be described hereinafter.

The walking gait cycle is broken down into 3 different phases:

(1) Contact phase: The outside of the heel hits the ground. Just after the heel strikes, "pronation" occurs. Pronation is when the foot flattens out and the ankle rolls inwards. At the same time, the lower leg rotates inwards from the knee down. The pronated foot is flexible and loose, serving as a shock absorber and allowing it to adapt to the ground just stepped on. The contact phase continues until the foot is completely flat on the ground.

(2) Midstance phase: The foot is flat on the ground and in this part of the gait cycle the body weight passes over the foot as the body comes forward. This is where the foot supports the body weight. The midstance phase is the part of the gait cycle where an abnormally functioning foot, such as an over-pronated foot (fallen arches) or an over-supinated foot (high arch foot) will typically manifest its problems. This phase ends as the body weight passes forward eventually forcing the heel to rise off the ground. At this stage "supination" occurs and the opposite to pronation happens: the muscles tighten and the foot becomes a rigid lever for the leg muscles to pull against. Rigidity in the foot should occur as the foot is propelled forward towards the next step. With supination, the foot rolls outwards and the lower leg rotates externally.

(3) Propulsion phase, also known as toe-off or lift-off: This is where the foot pushes off the ground to propel the body forward. Body weight is picked up by the ball of the foot and lastly the weight is absorbed by the big toe as you push off with that foot.

It is important to understand that both pronation and supination are part of a normal walking pattern. Pronation (rolling inward) acts as a shock absorbing process and supination (rolling outward) helps to propel the foot forward As forces on the foot attempt to flatten the arches during the foot contact phase of the gait cycle, the plantar fascia is stretched and tension on it is increased. During the propulsion phase (toe-off or lift-off) of the gait cycle the foot is used as a lever. During this phase, as the heel is raised from the ground surface, tension in the fascia often reaches its peak. A windlass mechanism formed by the fascia and its connection to the toes contributes to this increase in tension during the toe-off or lift-off (i.e. propulsion phase). The more aggressive the propulsion phase (e.g. during a sprint) the higher the peak stresses in the fascia.

The plantar fascia 110 is thick and essentially inelastic. If the tension on the plantar fascia 110 becomes excessive, the plantar fascia 110 may be damaged or injured and produce a condition called plantar fasciitis. Plantar fasciitis is a painful medical condition resulting from inflammation of the plantar fascia 110. Overstressing the plantar fascia 110 may produce tears in the plantar fascia 110 or separate the plantar fascia 110 from bone and other surrounding materials. Tearing and separation of the plantar fascia 110 produces inflammation which contributes to the intense pain experienced by plantar fasciitis sufferers, particularly after periods of rest. Frequently, the inflamed areas 305 are along the arch of the foot 100 and most often near the heel 101 of the foot as shown in FIG. 2, where the fascia has its smallest cross-sectional area.

Plantar fasciitis may be quite debilitating in that everyday activities such as walking and standing may be very painful. Typical treatments for plantar fasciitis may involve oral anti-inflammatories, ice packs, bedrest, stretching, steroid injections, night splints, wedge-shaped arch supports and compressive arch wraps. Even with these treatment options being employed many suffer in pain for periods of months. Plantar fasciitis cases extending beyond six months are not uncommon. The primary symptom is pain typically in the heel, experienced during the first few steps in the morning or after periods of rest. This pain is the result of inflammation accumulation in response to damaged tissue (i.e. micro-tears in the fascia). This inflammation which accumulates during rest, applies direct pressure to the damaged fascia and associated soft tissue, as one begins to stand, bear weight, or walk (i.e., apply load to the foot). The pain is often described as feeling like and ice pick in the heel. The pain is often described as feeling like and ice pick in the heel. The initial pain typically lessens after a few minutes of weight bearing as the fluid is pushed back into the surrounding tissue. The pain will continue to reoccur as long as damage to the fascia is allowed to continues or is prevented from healing by re-occurring stress. In extreme cases, treatment of plantar fasciitis may culminate in expensive and invasive corrective surgery. Plantar fasciitis is often experienced in only a single foot.

To gain access to the plantar fascia, surgeons may perform either an endoscopic procedure requiring small incisions or conventional direct visualization requiring the underside of the foot to be opened up. Both of which are painful, scars may result, and recovery time may be from weeks to months.

Improper treatment of plantar fasciitis may lead to other medical problems. For example, if inflammation near the heel is allowed to continue for a long period of time, calcium deposits may build-up in the damaged region. As the calcium builds-up, bony outcroppings, commonly referred to as "heel spurs" may develop in the heel. The longer the plantar fascia remains inflamed around the heel, the stronger the conditions are for the development of heel spurs. Protrusion of the heel spurs into the surrounding tissue may result in a cycle of irritation, inflammation, and pain known as heel spur syndrome. Heel spur syndrome is commonly treated with a surgical procedure requiring removal of the heel spurs from within the foot. An endoscopic procedure is typically not used for removal of heel spurs and open surgery is typically required. Recovery time from such surgery may range from weeks to months, during which time the patient has to curtail the amount of stress placed on the foot.

A common example of non-surgical treatment for plantar fasciitis is medical personnel strapping strips of adhesive tape to the bottom of an injured foot. Strips of tape are applied at various angles across the bottom of the foot. The adhesive tape is sold on rolls and is difficult to remove from the rolls and must be customized for application according to the imagination and skill of the person applying the tape. Typically, the tape cannot be effectively applied by the patient to the patient's own foot and usually requires application by another individual or a trained medical technician. The person applying the tape must cut off a section of the tape from a roll, cut the length of tape further into a therapeutic shape, and apply it to the patient. The cutting, shaping and positioning (tensioning) of the tape piece are left to the complete discretion of the person applying the tape, and it is a trial and error process. Even a trained medical technician must estimate a position, length, shape and degree of tension that will cause a subjective improvement in range of motion and pain relief in the patient. If the tapes are stretchable, this further complicates the application and decreases the likelihood of consistent and repeatable self-application. Care must also be exercised during the application of the tape to avoid blister-causing wrinkles in the tape and other problems. The tape, when subject to the cyclic tensile loads, looses effectiveness quickly as the materials elongate and the glue layers slip or creep. Multiple layers of material, glued to each other increase the opportunity for each or any of the glue layers to allow slippage as high tensile loads are applied. As the patient walks with the taped foot, the tape often works loose and stretches with time. Consequently, taping the foot is cumbersome, inefficient, and ineffective in preventing excessive stretching of the plantar fascia.

A popular commercially available high-stretch elastic adhesive tape known as KINESIO TEX™, is manufactured by Kinesio Co., Ltd. of Japan and disclosed in U.S. Pat. Nos. 5,861,348 and 7,902,420. This elastic tape is designed for maximum range of motion and provides 140% elasticity (about same as basic elasticity found in skin and muscles), allowing it to work with the body. It does not limit range of motion and ineffective in preventing excessive stretching of the plantar fascia. It is sold in rolls and also has the same disadvantages and tapping difficulties of other adhesive tapes as discussed above.

Another example of non-surgical treatment for plantar fasciitis is the use of elastic compression sock worn over the patient's foot or an elastic bandage or band worn around the mid-foot. These elastic devices exert compressive forces along the longitudinal and transverse axes of the patient's foot. While some patients may be willing to wear these elastic devices, they are inconvenient and cumbersome. In order to be installed on the foot, these elastic devices must be stretched to fit over the heel and toe or wrapped around the mid-foot. Because they are elastic, they allow the foot to move and stretch. Thus they have limited effectiveness in limiting the tensile stress on the plantar fascia, particularly during the propulsion phase of the gait cycle, as they do not limit deformation of the foot structure under load. Consequently, the plantar fascia may still be subjected to excessive tensile forces during the critical heeling process. Re-subjecting the plantar fascia to tensile forces before it has completely healed may re-aggravate damaged or injured portions of the plantar fascia and undermine the healing process. In addition, these elastic devices are meant to be worn multiple times and may require regular cleaning to avoid odors and foot infections. Also, they may not fit inside a shoe while being worn and may be considered unsightly or become contaminated while walking around without shoes.

DEFINITION OF TERMS

Before discussing other methods and existing foot support devices for treatment of foot disorders, it is believed that a definition of terminology and nomenclature used in the art would helpful in order to facilitate a better understanding of the significant differences and advantages of the present invention over existing orthotic and non-orthotic devices. The following terms, as used herein, have the following meanings.

With regard to materials, a "woven" fabric is that class of fabrics wherein involves the interlacing or interweaving of two sets of threads at right angles (perpendicular) to each other: the warp (lengthwise threads) and the weft (crosswise threads inserted over-and-under the warp threads). A woven fabric only stretches in the bias directions (45 degrees to its warp and weft threads). In contrast, a "non-woven" fabric is that class of fabrics wherein fibers or threads are matted together, usually in a random or non-directional manner, and are not held in place by interweaving. Felt and cardboard are examples of non-woven materials. The important technical difference between a woven and non-woven fabric is their tensile strength (i.e., resistance to elongation). Woven fabrics can have much higher tensile strength and resistance to deformation or elongation than that of non-woven fabric of the same GSM (Grams per Square Meter). The GSM is a scale for the weight of the sheet of fabric, paper, etc., which also provides some indication of its thickness. The term "microfiber" commonly refers to any fiber with strands less than 1 denier, or about half as thick as a strand of silk. Some microfiber fabrics use strands that are only 10 microns in diameter, or about one-tenth as thick as a human hair. "Denier" is the unit of measure for fibers that indicates their fineness.

With regard to thickness, the term "mil" is a unit of length or thickness, equal to one one-thousandth ($\frac{1}{1000}$) of an inch or 0.001". For example, 2 mils is equal to 0.002" ($\frac{2}{1000}$"). A "mil" is not the same as a "millimeter". In contradistinction, the term "millimeter", abbreviated "mm", is a unit of length or thickness, equal to one-thousandth of a meter or equal to thirty-nine thousandths ($\frac{39}{1000}$) of an inch. For example, 1 mm is equal to 0.039370 inches (approximately $\frac{3}{64}$"), and 2 mm is equal to 0.078740 inches (approximately $\frac{5}{64}$"). 1 mil is equal to 0.0254 millimeters (mm), and 1 millimeter (mm) is equal to 39.37007874 mils. As an example to compare the different thickness measurements; a sheet of standard 20 lb wt. copy paper and a common postage stamp are each about 0.1 mm (equal to 4 mils or 0.004 inches) thick, and a conventional postcard is approximately 0.178 mm (equal to 7 mils or 0.007 inches) thick.

With regard to material properties, the terms "resilient" and "elastic" refer to a material capable of regaining its original shape or position after being deformed elastically such as by bending, stretching, compression, or other deformation. "Deformation" is an alteration of shape, as by pressure or stress. "Resilience" is the capability of a strained body to recover its size and shape after deformation caused especially by compressive stress. The term "elasticity" is the physical property of a material that returns to its original shape after the stress (e.g. external forces) that made it deform is removed. The relative amount of deformation is called the "strain". The term "elongation" means the state of being elongated or lengthened. The term "stretch" means the elongation, lengthening, widening, or distending of a material under an applied load.

The term "modulus of elasticity" is the mathematical description of an object or substance's tendency to be deformed elastically (i.e., non-permanently) when a force is applied to it, more particularly, the ratio of the stress applied to a material to the resulting strain within the elastic limit, also known as "elastic modulus" or "tensile modulus". The term "tensile strength" is the measure of the ability of material to resist a force that tends to pull it apart. It is expressed as the minimum "tensile stress" (force per unit area) needed to split the material apart expressed as "psi" (lbs per square inch). It can be reported just as a force or as a force per unit width. Dimensions measured in the cross-machine (CD) direction are referred to as "width" dimension, while dimensions measured in the machine direction (MD) are referred to as "length" dimensions.

With regard to pressure sensitive adhesives (PSAs), the term "tack" is the property of an adhesive that enables it to instantly form a bond when brought into contact with another surface. The term "tack force", also called "tack strength", is the maximum force required to separate the bonded surfaces. "Adhesion" (peel adhesion), refers to how well the tape sticks to a surface. Usually measured in ounces of pull (force) required to remove a one-inch wide strip of tape from a steel plate (i.e., adhesion to steel), and expressed in ounces/inches. "Peel strength" is measured as a force required to remove a standard PSA strip from a specified test surface under a standard test angle (e.g., 90° or 180°) under standard conditions. Pressure sensitive adhesives (PSAs) may be "removable" or "permanent". "Low-tack" adhesives have low adhesion properties and are easily applied and removed (i.e. Post-It® notes) and generally can not support much weight, "Medium-tack" adhesives have high adhesion properties but are removable and repositionable, and "high-tack" adhesives are typically considered to be a relatively permanent bonding adhesive. Foil tape for HVAC duct work is an example of a permanent adhesive application.

The ASTM (the American Society for Testing and Materials), now named ASTM International, is an international standards organization that develops and publishes technical standards and testing methods for a wide range of materials, including various classes of pressure sensitive adhesive tapes. Such testing methods include Peel Adhesion, Shear Adhesion, Tensile Strength, Breaking Strength, Elongation, etc. For example, the average tensile strength in both the machine and cross-machine directions of each roll of tape shall be not less than 25 lbs/in (4.37 N/mm) of width; the average peel adhesion strength of each roll of tape shall be not less than 3.75 lbs/in (0.66 N/mm) of width. The average peel adhesion strength at a 180° angle of each roll of tape shall be not less than 3.75 pounds per inch (0.66 N/mm) of width of tape.

With regard to medical devices, medical dictionaries define a "splint" as a rigid or flexible appliance for fixation of displaced or movable parts (*Dorland's Medical Dictionary for Health Consumers*, © 2007 by Saunders); and an orthopedic device for immobilization, restraint, or support of any part of the body. It may be rigid or flexible (*Mosby's Medical Dictionary*, 8th edition. © 2009, Elsevier). An "orthopedic brace", also known as an "orthosis" or "orthotic", is a device used to: immobilize a joint or body segment, restrict movement in a given direction, assist movement generally, reduce weight bearing forces for a particular purpose, or otherwise correct the shape and/or function of the body to provide easier movement capability or reduce pain.

An "arch support" is an orthopedic shoe insert appliance having a molded shell placed inside a shoe to provide underside support for the foot. The molded appliance is flexible enough to provide comfort and rigid enough to support the arch of the foot. The shell can be custom milled to fit individual feet using a medical foot casting system, or generic shapes and sizes can be purchased based on foot size and arch height. Arch supports are commonly confused with another type of shoe insert known as "insoles", which offer added resilient padding for shock absorption.

As used herein in conjunction with the present invention, the term "orthotic" means a device for supporting and immobilizing a weak or injured joint or body segment, restricting movement in a given direction, assisting movement generally, reducing weight bearing forces, and improving the function of the joint or body segment to provide easier movement capability or reduce pain. The term "strap" means a long narrow flat strip of a flexible material used for securing, holding together, or wrapping. The term "disposable" means for use in a single continuous one-time application and treatment followed by removal and disposal, rather than for removal and re-use for additional or multiple applications. The term "non-resilient" means a non-cushioning material not capable of being deformed elastically, elongated, lengthened, widened, or distended by stretching or compressed by pressure or stress under an applied load. The term "inelastic" means a material not capable of being deformed elastically, elongated, lengthened, widened, or distended by stretching under an applied load or stress. The term "flexible" means capable of conforming to the shape and contours of the surface to which it is applied, and being flexed repeatedly without damage.

As used herein in conjunction with the present invention, the term "non-stretch" woven material means a woven material wherein both the warp (lengthwise) and weft (crosswise) threads are substantially inelastic; consequently, the fabric material is substantially non-stretchable beyond its original dimensions in a longitudinal and transverse direction. More specifically, a woven material which exhibits between 0% to 3% elongation along its longitudinal and transverse axis when adhered to a user's foot and subjected to applied foot loads and stresses during the phases of a walking gait cycle. The term "preformed" as used herein in conjunction with the present invention, refers to an object that has been formed during its manufacture into the condition or shape in which it is intended to be used prior to its use by an end user. This is in contrast to a sheet, strip, or roll, of material which requires cutting or shaping by an end user prior to its use.

As used herein in conjunction with the present invention, the term "mil" means a unit of length or thickness, equal to one one-thousandth (1/1000) of an inch or 0.001". 1 "mil" is equal to 0.0254 millimeters (mm) and thus is significantly smaller than 1 "mm", and should be clearly distinguished over the terms "millimeter" and "mm", which is a unit of length or thickness, equal to one-thousandth of a meter or equal to thirty-nine thousandths (39/1000) of an inch. 1 "mm" or "millimeter" is equal to 39.37007874 "mils", or 0.039370 inches (approximately 3/64") and, thus, is significantly larger than 1 "mil". As used herein in conjunction with the present invention, the term "ultrathin" means very thin; more specifically having a thickness less than 1 mm (less than 0.0394 inches).

Examples of Existing Orthotic Devices

There are many arch supports, insoles, cushions, and other devices which may be placed in shoes and merely sit under the arch of the foot to provide comfort or correct foot deformities, but do not restrict foot movement and are incapable of limiting plantar fascia stress during the entire walking gait cycle. These devices are simply ineffective in limiting tensile stress in the fascia as the heel lifts from the ground surface to propel the body forward.

There are also several patents that are directed toward various orthotic devices, arch supports, insoles, cushions, and other devices which are worn on, attached to, or stretched over a user's foot for preventing or treating foot injuries but are not effective in stabilizing the foot or reducing tensile stress on the plantar fascia during the propulsion phase of the gait cycle when the heel is elevated above the ground surface, or limiting deformation of the foot structure under load, and thus, have limited effectiveness in limiting tensile stress on the plantar fascia.

Domenico, U.S. Pat. No. 3,584,622, discloses a support member designed to prevent ankle injuries that is formed of flexible sheet material which includes a foot receiving member conforming generally in shape to the rear portion of a foot to receive the rear portion of a wearer's foot and cover the ankle, and stirrup portions extending upwardly from the foot receiving member to contact opposite sides of the wearer's leg, above the ankle. The inner surfaces of the foot receiving member and stirrups are provided with an adhesive coating for coupling the support to the foot and leg of a wearer. No part of the foot receiving member intrudes into the area of the calf muscles of the wearer, so that restriction of movement of the Achilles' tendon is avoided. Also, no part of the foot receiving member extends forwardly beyond the metatarsus (the middle part of the foot that forms the instep) of the wearer's foot, and the forward and upper portions of the foot receiving member are open to avoid restriction of desired foot movement. This device does not extend to the ball of the foot, allows movement of the Achilles' tendon, and allows foot movement, and would be incapable of protecting the plantar fascia from excessive stress during the phases of a walking gait cycle.

Roth, U.S. Pat. No. 5,840,053, discloses a supportive device for the longitudinal arch of the foot that applies a compressive force around the mid-foot comprised of a fabric-coated elasticized strap enclosing a specially designed pad of rubberized material. The strap is wrapped snugly around the longitudinal arch with the enclosed pad strategically placed under the longitudinal arch exclusively outside the lateral region of the plantar portion of the longitudinal arch, to provide optimum arch support and secured by a VELCRO-type fastener strip. The rubberized pad substantially regains its original thickness after compression for absorbing energy and defending against shock, the longitudinal axis of the pad is approximately perpendicular to the longitudinal axis of the foot, and has a tapered portion disposed from the longitudinal axis of the foot toward the medial region of the longitudinal arch to minimize effects of pronation (rolling inward of the foot and ankle).

Examples of Existing Non-Orthotic Devices

There are also several patents that are directed toward various non-orthotic devices known in the art that are worn on, or attached to, a user's foot that merely provide a cushion for comfort or protect the foot from contact with floor surfaces of indeterminate cleanliness and temperature. These types of devices do not limit deformation of the foot structure during the phases of the walking cycle and, thus, are incapable of or ineffective in limiting tensile stress on the plantar fascia during the walking phases.

For example, Burgess, U.S. Pat. No. 6,640,465, discloses a lightweight removable and disposable foot protector that protects the wearer's foot when walking across surfaces that may be unsanitary, cold, wet, hot, slippery or otherwise undesirable. The foot protector includes a resilient sheet member having a shape generally matching a shape of a sole of a foot and a size generally corresponding to a size of the foot. The resilient sheet member has a foot-contact surface with a tack adhesive layer on at least a portion of the foot-contact surface. The resilient foot protector allows increased mobility of the foot when adhered thereto. The thickness of the foot protector is in the range of about 1 mm (equal to 39.370 mils or 0.039 inches or approximately 3/64", to about 5 mm (equal to 196.850 mils or 0.197 inches or approximately 13/64", a little over 3/16"), with a preferred thickness of about 2 mm (equal to 78.740 mils or 0.079 inches or approximately 5/64", a little over 1/16"), to provide enough resilience, or cushion effect, to provide comfort to the foot of the wearer. Burgess teaches that the adhesive is a relatively low-tack adhesive, for example, adhesives used in BAND-AIDS™, POST-IT NOTES™, feminine pads, and the like, which is sticky enough to hold the foot protector against the foot, but allows easy removal of the foot protector from the sole of the foot. Burgess teaches that the easier it is to remove the foot protector from the sole of the foot, the more the wearer can experience the comfort level of a conventional slipper. Burgess also teaches that the resilient sheet may be formed by a corrugated sheet interposed between two flat sheet members, such as cardboard, or other corrugated materials, such as corrugated plastics, or formed by a fibrous layer or foam rubber and that the fibers of the layer may be synthetic fibers, such as polypropylene fibers, or natural fibers, such as paper or cloth fibers; or a multi-layered resilient foam rubber layer or fibrous layer sandwiched between external layers of synthetic or natural material, Preferably, the fibers are randomly oriented (i.e. non-woven) to provide a good degree of resilience and flexibility. An exemplary material is a spunbond polypropylene, such as that described in U.S. Pat. No. 4,801,494 to Datta et al (directed toward a non-woven absorbent fabric that provides fast absorbency of bodily exudates for use as a liner in feminine napkins, absorbent garments, diapers, etc.).

Holden, U.S. published Patent Application 2004/0006814 discloses protective peel and stick adhesive pad attachments for protection and decoration that removably attach to the bottom of the human foot, to the human hands, elbow, knees, shins, and also to animal foot pads, in a snug tight fit. These pads offer foot protection for walking at the beach or poolside, and may be used in some sports such as surfing, swimming, beach volleyball, river rafting, boating, dance, aqua aerobics, and gymnastics. The adhesive used by Johnson & Johnson in its hydrocolloid adhesive Band-Aid® Callus Relief product featuring Compeed® Moisture Seal™ Technology is among the preferred adhesives. The adhesive used in Dr. Scholl's® Waterproof Corn Cushions is more preferred, especially for applying toe pieces on the bottoms of the toes. MSX 5527 PU acrylate adhesive tape with polyurethane backing by 3M is most preferred, especially for applying toe pieces on the bottoms of the toes.

Examples of Existing Pressure Sensitive Adhesive Tapes

There are also several patents that are directed toward industrial pressure sensitive adhesive (PSA) tapes for industrial applications having high tensile strength that meet Underwriter Laboratories requirements and the ASTM technical standards and testing methods for their particular class of tapes. These industrial tapes are supplied in rolls and are not particularly suitable for orthopedic use or for application to human skin.

For example, Desnoyers, U.S. Pat. No. 3,482,683 discloses a thin flexible normally tacky pressure sensitive bundling tape having relatively high longitudinal extensibility and high resistance to crosswise tearing forces which will not delaminate, split or fibrillate when unwound from a roll. The tape comprises a relatively thin backing film, a normally tacky and pressure-sensitive adhesive coating on one surface of the backing film and a delamination resistant secondary layer united to the other surface of the backing film. The backing film comprises a hypermolecularly oriented linear crystalline polyolefin film consisting essentially of molecular chains that are predominantly oriented lengthwise of the tape in the form of a series of longitudinally extending fibrous polyolefinic elements which are coherently assembled in the film and undistinguishable to the naked eye. The hypermolecularly oriented backing film has a tensile strength in the lengthwise direction of at least about 20,000 psi and a ratio of lengthwise elongation at break to crosswise elongation at break of at least about 10 to 1 and a ratio of lengthwise tensile strength to crosswise tensile strength of at least about 3 to 1. The delamination resistant secondary layer has a lengthwise resistance to tearing that is greater than the lengthwise resistance to tearing of the backing film.

Huddleston et al, U.S. Pat. No. 4,997,709 discloses an adhesive foil tape for use with rigid fiberglass air ducts that meets Underwriter Laboratories, Inc. 181A requirements and specifications for aluminum or aluminum foil tapes for use with rigid fiberglass air ducts, and the applicable ASTM technical standards and testing methods outlined in ASTM D3759, ASTM 3330, and ASTM D3654. The tape has a metal foil backing carrying a layer of an adhesive composition consisting essentially of: (1) 100 phr of a block copolymer consisting of from 75 to about 100 parts by weight of a styrene-isoprene-styrene triblock copolymer and from 0-25 parts by weight of a member selected from the group consisting of a styrene-isoprene diblock copolymer, a styrene-butadiene-styrene triblock copolymer and a mixture of styrene-isoprene diblock copolymer and styrene-butadiene-styrene triblock copolymer; (2) from about 60 to about 110 phr of rubber phase associating resin; (3) from about 5 to about 30 phr of a polyestyrene phase associating resin; (4) an effective amount of flame retardant; (5) an effective amount of antioxidant for the rubbery isoprene moiety; and (6) a crosslinking system for crosslinking the isoprene moiety.

SUMMARY OF THE INVENTION

The present invention overcomes the aforementioned problems and is distinguished over the prior art in general, and these patents in particular by a disposable two-part orthotic foot support strap system having a sole support strap member and an arch support strap member that can be adhesively applied to a foot individually or in combination for reducing tensile loads and stresses and providing anatomical support and stability to the musculoskeletal system and the sole, arch and heel of a foot of a user, and relief from plantar fasciitis. The sole support strap is a preformed elongate generally rectangular ultrathin strap formed of flexible, non-resilient non-stretch woven material having an adhesive layer on an underside surface thereof, the underside surface having a contiguous ball of foot portion, a midfoot portion, and a heel portion adapted to be adhered to, and extend along, the ball of the foot, the midfoot, and the heel of the user's foot, and conform to the curvature thereof. In a preferred embodiment, a pair of elongate laterally spaced heel tabs extend rearwardly from the heel portion to be adhered to the back side and lateral sides of the back of the user's heel in crossed over relation to one another to form a generally cup-shaped cradle configuration conforming to the contours of the back side of the user's heel to prevent slippage of the sole support strap. The arch support strap is a preformed elongate generally rectangular ultrathin strap formed of flexible, non-resilient non-stretch woven material having an adhesive layer on an underside surface thereof adapted to be adhered transversely over the midfoot portion of the sole support strap and at least a portion of opposed sides of the arch of the user's foot and conform to the curvature thereof.

In a preferred embodiment, the non-stretch woven material is a woven material formed of synthetic microfibers, and has a tensile strength sufficient to prevent stretching and elongation of the sole support strap and the arch support strap in a longitudinal and transverse dimension, and the adhesive layer of each has a tack strength sufficient to prevent slipping or creeping.

In the adhered condition on the skin surfaces of the foot, the sole support strap flexes with the foot, and when subjected to cyclic loading and stresses during phases of a walking gait cycle, functions as a tensile load bearing member, in the manner of an external ligament, in the region between the ball of the foot and the heel of the foot to reduce fascia stress throughout the gait cycle, and particularly peak tensile loads and stresses in the plantar fascia by maintaining an essentially constant distance between the ball of the foot and the heel of the foot during a heel contact phase, a weight bearing mid-stance phase, and a propulsion (toe-off or lift-off) phase of the walking gait cycle so as to bear major tensile loads and stresses, which would otherwise be absorbed primarily by the plantar fascia as forces on the foot attempt to flatten the arch. The arch support strap, when used in combination with the sole support strap, in the adhered condition, maintains the sole support strap in adhesive engagement with the sole of the user's foot and provides additional support to the arch and the bone structure of the user's foot to reduce tension and stretching of the arch and plantar fascia during the pronation and propulsion phases of the gait cycle. The arch strap functions synergistically with the sole strap. Encircling the mid-foot, with the arch strap over the sole strap prevents the sole strap from pulling loose in the arch area of the mid-foot as the arch strap is under tension, thus assisting the sole strap in functioning in a manner much like the underlying plantar fascia. The non-stretch material of the arch strap and slip resistant bond with the skin surface enables it to provide direct support to the arch and to the stabilize the bones of the mid-foot. The arch support strap may also be used alone to provide stability and support to the arch and the bone structure of the user's foot to reduce tension and stretching of the arch and plantar fascia during the pronation and propulsion phases of the gait cycle.

The ultra-thin non-stretch materials of the sole support and arch support straps allow them to be applied without adding bulk or applying circulation constraining compression. The non-slip adhesive bond allows strain on the foot to be transferred via the skin layer to the non-stretch material thus providing a ligament-like level of support.

One of the significant features and advantages of the present foot support strap system is that that the sole support strap functions as a tensile load bearing member, in the manner of an external ligament, in the region between the ball of the foot and the heel and, because it is securely affixed and substantially inelastic, effectively reduces fascia stress through the entire gait cycle, and particularly reduces peak stress in the plantar fascia by maintaining the distance between the ball of the foot and the heel of the foot constant during the heel contact phase, the weight bearing midstance phase, and the propulsion (toe-off or lift-off) propulsion phase of the walking gait cycles; thus, bearing or sharing major tensile loads and stresses, which would otherwise be absorbed primarily by the plantar fascia, and the fascia and surrounding tissues across both the medial and longitudinal arches, to prevent damage to the fascia and allows damaged fascia to heal.

Another feature and advantage of the present foot support strap system is that the arch support strap may be used in combination with the sole support strap to effectively maintain the sole support strap in adhesive engagement with the sole of the foot and prevent it from pulling loose in the arch area of the foot, or may be used alone to provide anatomical structural support to the arch, the mid-foot, and the bone structure of the foot, to limit pronation or prevent over pronation of the foot.

Another feature and advantage of the invention is that the sole support strap restricts extension of the tissue on the bottom of the foot to significantly reduce the level of tensile stress on the plantar fascia to reduce foot pain, arch pain, and heel pain, and rehabilitate the plantar fascia, and prevent further injury to the plantar fascia Another feature and advantage of the invention is that the sole support strap includes heel tabs that, in a preferred embodiment, can be adhered to the back side and lateral sides of the back of the heel in a crossed configuration to provide a generally cup-shaped cradle for the heel, provide resistance to slippage, and when bonded to the outer skin surface at the back of the heel directs tensile stresses around and away from the center of the heel to protect an area of the plantar most likely to be injured.

Another feature and advantage of the invention is that it provides durable support and minimizes plantar stresses through the entire walking gait cycle and allows a user to limit stress on the foot while continuing with most normal activities, including running, sports and other activities.

Another feature and advantage of the invention is that the sole support strap restricts extension of the tissue on the bottom of the foot to significantly reduce the level of tensile stress on the plantar fascia to reduce foot pain, arch pain, and heel pain, and rehabilitate the plantar fascia, and prevent further injury to the plantar fascia Another feature and advantage of the invention is that the sole support strap and the arch support strap are ultrathin and closely conform to the shape and contours of the foot, and can be worn alone or in combination inside shoes, socks and hose without being easily detected or causing uncomfortable bulk, and can also be worn while using other foot support devices such as arch supports, night splints, and custom orthotics.

Another feature and advantage of the invention is that the sole support strap and the arch support strap employ woven microfiber materials and high tack strength adhesive which allow them to be worn for many hours during normal and rigorous activities, without deforming or slipping position on the skin surface.

Another feature and advantage of the invention is that the woven microfiber material substantially prevents stretching and elongation of the sole support strap and spreads shear stresses over a large surface area without exceeding the adhesive limits of the adhesive.

Another feature and advantage of the invention is that the sole support strap and arch support straps are preformed and shaped and sized to fit most foot sizes without modification, are easily and quickly installed by the user and, if desired, can be easily trimmed with a pair of scissors to fit a particular user or foot irregularity.

Another feature and advantage of the invention is that the support strap system may worn by a user who is not currently experiencing pain, but anticipates the potential for injury during a strenuous activity or exercise, and wishes to avoid overstressing the plantar fascia.

Another feature and advantage of the invention is that the sole and arch straps are preformed, pre-cut and pre-shaped and include removable cover sections over their adhesive layer enabling easy and consistent self application without handling adhesive surfaces by an end user, and without requiring special training, professional skills, extensive modification, or use of tools.

Another feature and advantage of the invention is that the sole and arch straps are preformed and shaped for universal application to a right or left foot, and provide ease and consistency of self-application.

Another feature and advantage of the invention is that it provides a method of treating heel pain and plantar fasciitis by limiting damaging stress in the fascia through the entire walking cycle and for extended periods of time from hours per day to multiple days in a row, both at times with and without footwear thus allowing the fascia a therapeutic duration of rest in order for healing to occur uninterrupted by high tensile stress.

Another feature and advantage of the invention is that it can be use by a person who is not currently experiencing pain, but anticipates the potential for injury during a strenuous activity or exercise, and wishes to avoid overstressing the plantar fascia.

A further feature and advantage of the present invention is that the level of support provided by the system can be easily adjusted by a user by altering the degree of dorsal flexion about a 90° (neutral dorsal flex) position during application in order to produce the desired level of support.

A still further feature and advantage of the invention is that the support strap system is simple in construction, inexpensive to manufacture, and extremely rugged and durable in use.

Other features and advantages of the invention will become apparent from time to time throughout the specification and claims as hereinafter related.

DESCRIPTION OF THE PREFERRED EMBODIMENTS

The present invention is a disposable two-part non-resilient, non-stretch orthotic foot support strap system having a sole support strap member 10 and an arch support strap member 20 that can be adhesively applied to a foot individually or in combination to reduce tensile loads and stresses and provide anatomical support and stability to the musculoskeletal system and the sole, arch, and heel of a foot of a user, and relief from plantar fasciitis.

Figure 3:
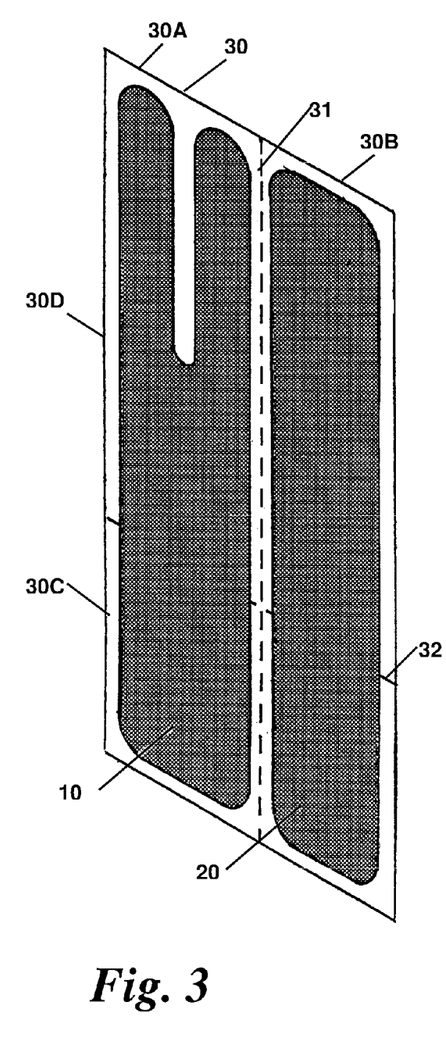
FIG. 3 is a perspective view of the sole support strap member and arch support strap member of the disposable two-part non-resilient, non-stretch orthotic foot support strap system in accordance with the present invention removably adhered to the front side of a release liner sheet.
Figure 4:
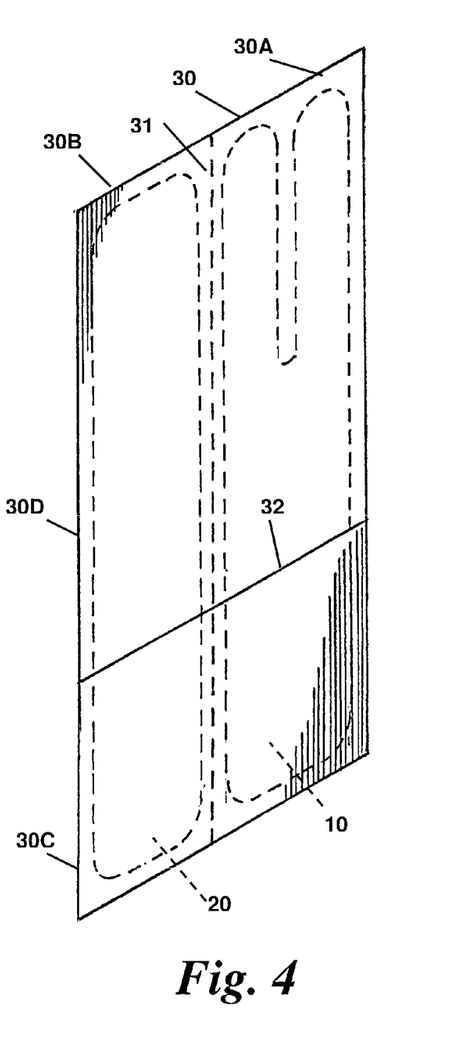
FIG. 4 is a perspective view of the back side of the release liner sheet showing the perforated line extending between the sole support strap and the arch support strap and the transverse cuts that extend across the underside of the sole support strap and arch support strap.

Referring now to FIGS. 3 and 4, in a preferred embodiment, the sole support strap 10 and the arch support strap 20 are removably adhered to a generally rectangular release liner sheet 30 in laterally spaced relation. The release liner sheet 30 is formed of thin paper or plastic film coated on one side with a release agent, such as for example silicone, and the adhesive side of the sole support strap 10 and the arch support strap 20 are adhered to the coated side of the release liner sheet. The construction of the sole support strap 10 and the arch support strap 20 and their structural properties will be described in detail hereinafter.

The release liner backing sheet 30 may be perforated along a straight line 31 extending longitudinally from end to end between the sole support strap 10 and the arch support strap 20 to provide separate releasable portions 30A and 30B, and provided with a transverse cut 32 that extends between the longitudinal sides of the sheet.

The perforated line 31 allows the sole support strap 10 and the arch support strap 20 to be separated but still adhered to respective longitudinal portions 30A, 30B of the release liner sheet 30, and with a respective transverse cut 32 extending across the adhesive side of the sole support strap 10 and the arch support strap 20 intermediate their opposed ends. The separated portions of the of the release liner backing sheet 30 prevent accidental adhesion prior to use. The cut 32 defines first and second shorter segments 30C and 30D of the longitudinal portions of the release liner sheet 30, that can be removed individually from the adhesive side of the sole support strap 10 and the arch support strap 20, respectively, as described hereinafter. The release liner backing sheet 30 may formed of various commercially available release liner materials such as for example, but not limited thereto, a 3.5 mil 60 lb. KRAFT™ release liner paper.

It should be understood that, alternatively, the sole support strap 10 and the arch support strap 20 may be provided individually with each adhered to a respective longitudinal strip of a release liner sheet 30 with each strip having a respective transverse cut 32 extending across the adhesive side of the sole support strap 10 and the arch support strap 20 defining first and second shorter segments 30C and 30D of the longitudinal release liner sheet 30, that can be removed individually from the adhesive side of the sole support strap and arch support strap.

Figure 5A:
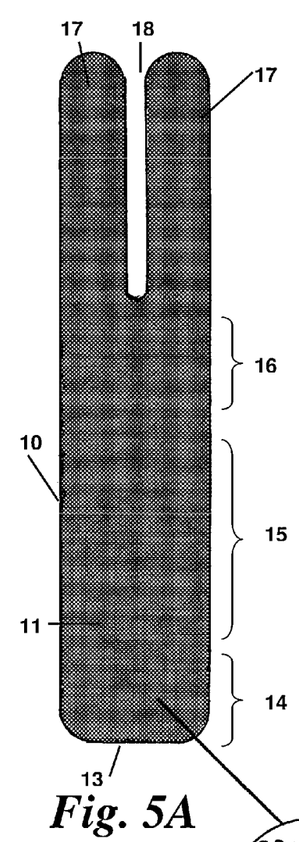
FIGS. 5A, 5B, and 5C are a front elevation view, a side view, and a rear elevation view, respectively, of the sole support strap.
Figure 5B:
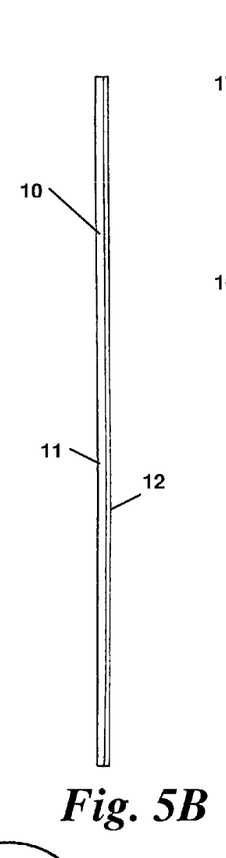
Figure 5C:
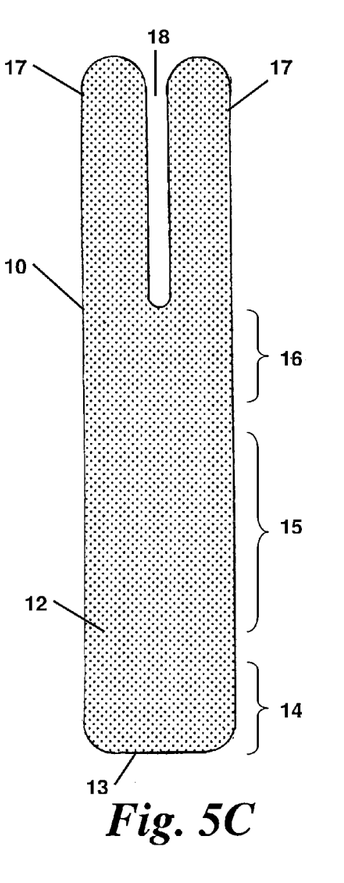

Referring now to FIGS. 5A, 5B, and 5C of the drawings by numerals of reference, there is shown, a preferred sole support strap member 10 formed of an ultrathin ply of flexible, non-resilient non-stretch woven material 11 having an adhesive layer 12 on one side (described in detail hereinafter). The sole support strap 10 is preformed and has an elongated, generally rectangular shape preferably with rounded corners. The underside of the sole support strap 10 includes a front end 13, and a contiguous ball of foot area 14, mid-sole area 15, and heel area 16, with integrally formed laterally spaced apart heel tabs 17 extending a distance rearwardly from the heel area. Preferably, each of the heel tabs 17 has a generally rectangular configuration with rounded outer ends, and are disposed in parallel relation separated by an inwardly extending cut 18. It should be understood that, alternatively, the heel tabs 17 may be formed as a single strip perforated along a central straight line, and manually divided. It should also be understood that the heel tabs 17 may be of other configurations, and may not be parallel.

In a preferred embodiment, for use by an adult, the sole support strap 10 has an overall length in the range of from about 6.0 inches to 14.0 inches, more preferably, in the range of from about 9 inches to 12 inches, and most preferably a length of about 10 to about 11.5 inches.

In a preferred embodiment for use by an adult, the sole support strap 10 has a width in the range of about 1 inch to about 3.5 inches, more preferably, in the range of from about 2.0 inches to about 3.00 inches, and most preferably a width of about 2.25 inches. The sole support strap 10 does not need to be as wide as a user's foot nor cover the entire fascia of the user to be effective. Preferably, the sole support strap 10 has a length to width ratio greater than 2.5, more preferably, a ratio greater than 3.5, and most preferably a ratio of about 4.5.

The heel tabs 17 are preferably of a length in the range of from about 1.0 inches to about 6.0 inches, more preferably a length of about 3.0 inches to about 4.0 inches, and most preferably a length of about 3.75 inches, or a length of about one-third the length of the sole support strap 10. Each heel tab 17 has a width in the range of about 0.375 inches to about 1.75 inches, more preferably, in the range of from about 0.875 inches to about 1.5 inches, and most preferably a width of about 1 inch.

As described hereinafter, when applied to the user's foot, the sole support strap 10 extends along the sole of the foot from the ball of the foot to the heel, excluding the toes, and the heel tabs 17 are crossed over the back side and lateral sides of the back of the foot forming a cradle to support the heel and further insure against slippage. The divided heel tabs allow the sole support strap 10 to be used on a wide range of foot sizes. The heel tabs will simply extend further up the back of a smaller foot and extend less on larger feet.

Figure 6A:
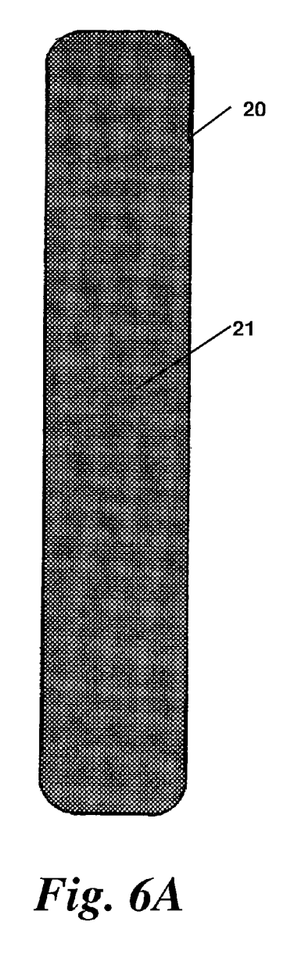
FIGS. 6A, 6B, and 6C are a front elevation view, a side view, and a rear elevation view, respectively, of the arch support strap.
Figure 6B:
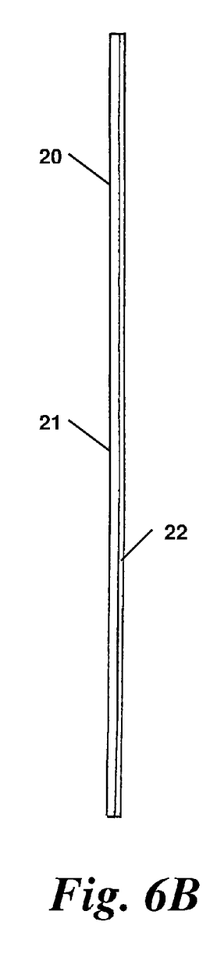
Figure 6C:
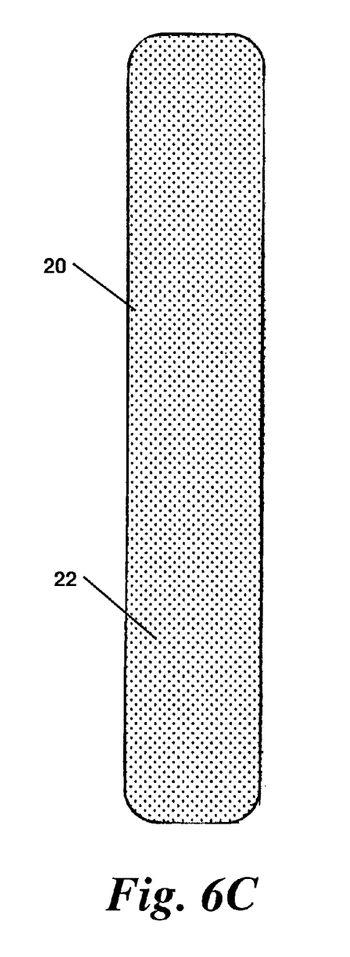

Referring additionally to FIGS. 6A, 6B, and 6C, the arch support strap member 20 may be used in combination with the sole support strap member 20 to supplement and further aid in supporting the foot and particularly the plantar fascia, and to minimize pronation of the foot. The arch support strap 20 when applied transversely around and over the outside of the foot sole support strap member 10 is effective in maintaining the sole support strap 10 in adhesive engagement with the sole of the foot, and prevents it from pulling loose in the arch area of the foot, thus assisting the sole support strap member in maintaining proper tension. The arch support strap 20 is also effective in limiting pronation or preventing over pronation, as it provides support to the arch and the bone structure of the foot. The arch support strap 20 may also be used alone without sole support strap 10 to provide anatomical support to the mid-foot foot and particularly to prevent or limit pronation.

The arch support strap 20 is formed of formed of an ultrathin play of flexible, non-resilient non-stretch woven material 21 having an adhesive layer 22 on one side (described in detail hereinafter). The arch support strap 20 is precut and has an elongated, generally rectangular shape preferably with rounded corners.

In a preferred embodiment, the arch support strap member 20 has a length in the range of from about 6 inches to about 14 inches, more preferably, in the range of from about 9 inches to about 12 inches, and most preferably a length of about 10 to about 11.5 inches. In a preferred embodiment for use by an adult, the arch support strap 20 has a width in the range of about 0.75 inch to about 3.5 inches, more preferably, in the range of from about 1.0 inches to about 3.0 inches, and most preferably a width of about 1.5 inches to about 1.75 inches. The arch support strap 20 may wholly encircle the arch area of the foot, but does not need to cover the entire arch.

The preformed generally rectangular configuration of the sole support strap 10 and arch support strap 20 is preferable because it allows them to be used universally on either a left foot or a right foot. The rectangular shape also provides ease of use and of manufacture. The rounded corners are preferable because they significantly reduce or eliminate the possibility of the corners becoming snagged and accidentally peeling up. It should be understood, however, that the sole support strap 10 and arch support strap 20 may be provided in other shapes and dimensions. They may also be easily cut or trimmed by the user into a desired shape for a particular preference.

Figure 5D:
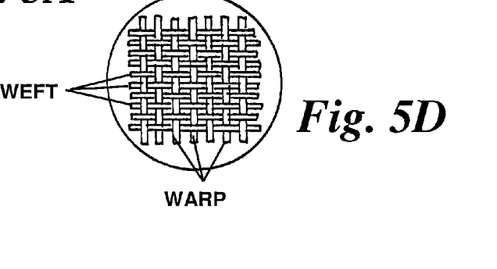
FIG. 5D is an enlarged detail of a portion of the sole support strap showing, somewhat schematically, the warp and weft pattern of the non-stretch woven material of the sole support strap.

A preferred material suitable for use in constructing the ultrathin ply of flexible, non-resilient non-stretch ply of woven material 11 and 21 of the sole support strap 10 and the arch support strap 20 is a woven microfiber using synthetic microfibers, such as, for example rayon microfibers, wherein both the warp (lengthwise) and weft (crosswise) microfibers (FIG. 5D) are substantially inelastic; consequently, the woven material is substantially non-stretchable beyond its original dimensions in a longitudinal and transverse direction. The ultrathin ply of woven material 11 and 21 of the sole support strap 10 and the arch support strap 20 has a thickness less than 1 mm; preferably in a range of between about 5 mils (0.127 mm or 0.005 inch) to about 30 mils (0.762 mm or 0.030 inch), and most preferably less than 15 mils (0.381 mm or 0.015 inch). This woven microfiber material has a tensile strength in excess of 70 lb/in-width and a ratio of elongation-to-tensile strength that is less than nine tenths (0.9) to provide a balanced combination of strength and resistance to elongation. It should be understood that other flexible non-resilient non-stretch woven materials having these same or substantially the same physical properties may be used.

The thin flexible non-resilient non-stretch material of the sole support strap 10 and the arch support strap 20 may also be breathable. For example, the material may have a moisture vapor transfer rate (MVTR) of at least 100 g/24 h/m$^2$. The flexible non-resilient non-stretch material of the sole support strap 10 and the arch support strap 20 may also be a hypo-allergenic material.

The pressure sensitive adhesive layer 12 of the sole support strap 10 and adhesive layer 12 of the arch support strap 20 is a high holding strength adhesive of sufficient tack strength so as to adhere the sole support strap 10 and arch support strap 20 to the user's foot during periods of activity but allow them to be removed without damage to the user's skin. A preferred pressure sensitive adhesive suitable for use is an adhesive having a 180° peel strength equal to, or greater than, 15 oz/in when tested in accordance with the Pressure Sensitive Tape Council (PSTC) PSTC-3 Standard Adhesion to Steel 180° Peel Test. The preferred adhesive is also hypo-allergenic and non-irritating to the skin. Preferably, the adhesive layer 12, 22, is less than 3.5 mils (0.0889 mm or 0.0035 inch) thick. The adhesive 12, 22, allows the sole support strap 10 and the arch support strap 20 to be easily removed and readjusted by pulling the support strap member in a direction away from the skin surface, such as when pulled at a ninety-degree angle from the skin surface. The adhesive having these properties is highly resistant to shear stresses and will not allow the foot support strap 10 and arch support strap 20 to slip or creep under cyclic loading and stresses during use.

The combined thickness of the non-resilient non-stretch woven material 11, 21, and adhesive layer 12, 22, is less than 1 mm; preferably in a range of between about 5 mils (0.127 mm or 0.005 inch) to about 30 mils (0.762 mm or 0.030 inch), and most preferably less than 15 mils (0.381 mm or 0.015 inch).

The thin flexible non-resilient non-stretch woven material 11, 21, and adhesive 12, 22, of the sole support strap 10 and the arch support strap 20 meets the ASTM technical standards and testing conditions outlined in ASTM D3759, exhibiting less than 15% elongation when subject to a 25 pound tensile load. The sole support strap 10 and the arch support strap 20 each preferably have a ratio of elongation-to-tensile strength (lb/in-width) that is less than nine tenths (0.9) to provide a balanced combination of strength and resistance to elongation.

Preferably, the tensile strength (lb/in-width) of the sole support strap 10 and the arch support strap 20 is greater than 15 lb/in-width and more preferably greater than 25 lb/in-width. During use, the forces on the sole support strap 10 may exceed 15 lbs, and the sole support strap 10 and the arch support strap 20 will exhibit less than 3% or no elongation when adhered to a user's foot and therefore would be essentially inelastic along its longitudinal and transverse axis when subjected to a 15 lb force and not capable of being deformed elastically, elongated, lengthened, widened, or distended by stretching under the applied foot loads and stresses during the phases of the walking cycle.

Thus, the inelastic non-stretch properties of the woven microfiber material 11, 21, of the sole support strap 10 and the arch support strap 20 combined with the "adhesion" and "peel strength" properties of the adhesive 12, 22, provide a sole support strap 10 and arch support strap 20 that are highly resistant to shear stresses, and will not tear, stretch or elongate, and will not slip or creep under cyclic loading and stresses during the phases of the walking cycle. When properly applied, the sole support strap 10, functions as a tensile load bearing member, in the manner of an external ligament, in the region between the ball of the foot and the heel. Because the sole support strap 10 is substantially inelastic or non-stretchable, it effectively reduces fascia stress through the entire gait cycle, and particularly reduces peak stress in the plantar fascia by maintaining the distance between the ball of the foot and the heel of the foot constant during the heel contact phase, the weight bearing midstance phase, and the propulsion (toe-off or lift-off) propulsion phase of the walking gait cycles; thus, bearing or sharing major tensile loads and stresses, which would otherwise be absorbed primarily by the plantar fascia, and the fascia and surrounding tissues across both the medial and longitudinal arches, to prevent damage to the fascia and allows damaged fascia to heal. The elasticity of the skin surfaces at the back of the heel to which the crossed heel tabs 17 are adhered aid in preventing the non-stretch sole support strap 10 from slipping or pulling loose under the applied foot loads.

The arch support strap 20, when used in combination with the sole support strap 10, is adhered transversely over the outside of the foot sole support strap member 10, and at least partially over the sides of the arch, and is effective in maintaining the sole support strap 10 in adhesive engagement with the sole of the foot and prevents it from pulling loose in the arch area of the foot, thus assisting the sole support strap member in maintaining proper tension, and also supplements and further aids in supporting the foot and particularly the plantar fascia, and minimizes pronation of the foot (rotation of the medial bones in the midtarsal region of the foot inward and downward). When used alone, the arch support strap 20 is adhered transversely under the arch of the foot and at least partially around the outer sides thereof, and provides anatomical structural support to the arch, the mid-foot, and the bone structure of the foot, and limits pronation or prevents over pronation.

The flexibility and extreme thinness features of the sole support strap 10 and the arch support strap 20 allow them to conform to the shape and contours of the human foot, and also allows them to be worn alone or in combination inside shoes, socks and hose without being easily detected or causing uncomfortable bulk. The present orthotic foot support system allows a user to limit stress on the foot while allowing the user to continue with most activities, including running, sports and other activities. The support strap system can also be worn while using other foot support devices such as arch supports, night splints, and custom orthotics.

Application to the Foot

Referring now to FIGS. 7A-7G, the method of applying the sole support strap 10 and the arch support strap 20 to the foot will be described. For best results, it is recommended that the foot be washed and thoroughly dried prior to application and that the user be seated to apply the straps.

Figure 7A:
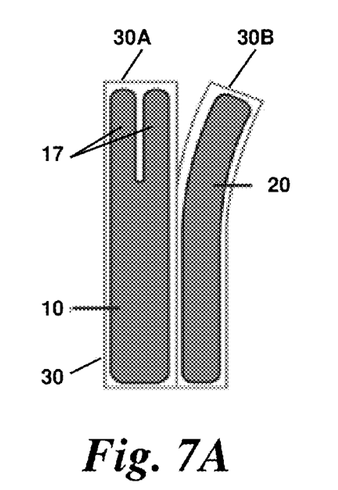
FIGS. 7A through 7H are illustrations showing the steps of separating and removing the sole support strap and the arch support strap, applying the sole support strap to the sole of a wearer's foot, adjusting the tension, securing the heel tabs, and applying the arch support strap around the arch and over the outside of the foot sole support strap, or around the arch of the foot.

The release liner backing sheet 30 is torn along the longitudinal perforated line 31 to separate the respective first and second longitudinal portions 30A, 30B with the sole support strap 10 and the arch support strap 20 still adhered to the respective longitudinal portions release liner sheet (FIG. 7A).

Figure 7B:
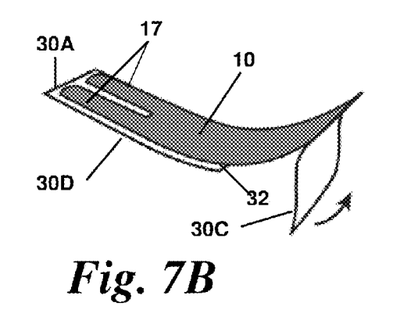

The first longitudinal portion 30A of the release liner backing sheet bearing the sole support strap 10 is bent along the transverse cut 32 so as to expose the facing edges of the first and second shorter segments 30C and 30D of the longitudinal release liner backing sheet portion 30A. The edge of the first shorter segment 30C is gripped and peeled off to expose the adhesive side of the sole support strap 10 (FIG. 7B).

Figure 7C:
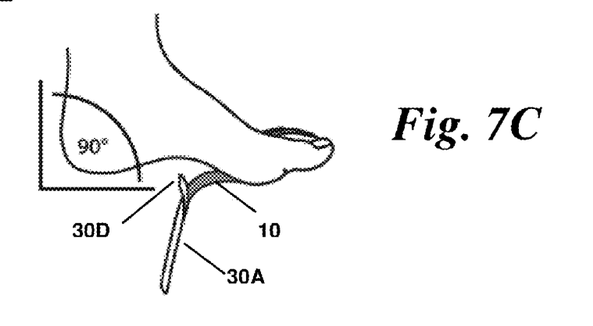

The front or ball of foot portion of the sole support strap 10 is pressed onto the ball of the foot just behind the toes. It is beneficial that this portion be applied first, as it allows the tension in the sole support strap to be preloaded as described hereinafter. With the sole support strap 10 attached to the ball of the foot, the foot is positioned at neutral 90° angle or slightly downward. The degree of downward angle affects the level of tension and degree of support to be afforded by the sole support strap. The second shorter segment 30D of the longitudinal release liner backing sheet portion 30A is gripped and peeled off to expose the adhesive side of the remaining portion of the sole support strap 10 (FIG. 7C).

If the sole support strap 10 is applied while the foot is in dorsal flexion, the resulting tension of the sole support strap will be low. If the sole support strap is applied in plantar flexion, the resulting tension will be higher as the foot tries to straighten out. Thus, the tension can be adjusted by the position of the foot while the sole support strap is being applied to the foot.

More specifically, the method of controlling tension in the support strap system includes (1) holding ones foot in a generally neutral flex position (about a 90° angle relative to the shinbone) during application of the sole support, particularly as it is being adhered along the longitudinal axis of the foot; and/or (2) increasing the angle (plantar flexion) or decreasing the angle (dorsal flexion) to an alternative angle correspondingly increasing or decreasing the desired degree of support provided by the sole strap. Alternately, one may apply the sole strap, take a step to test the degree of support, then detach and reapply the arch strap with the desired pre-tension by adjusting the angle or degree of flexion. The initial degree of flexion is preferably 90° degrees plus or minus 15° degrees. The degree of plantar flexion above 90° is preferred to much less than 30 degrees, for a resultant angle typically not exceeding 120° degrees.

Figure 7D:
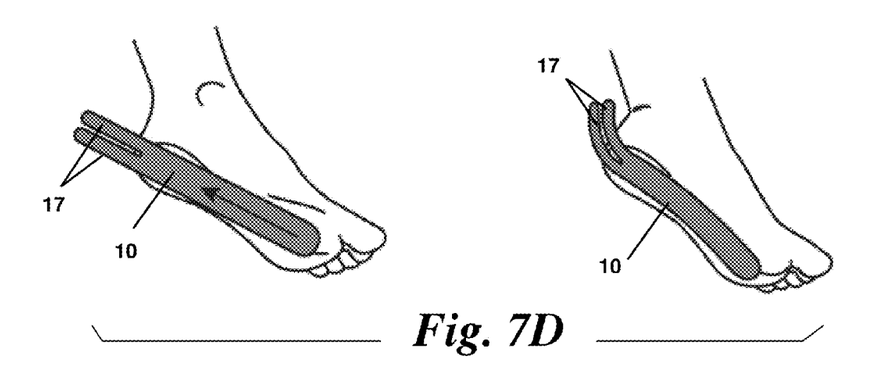

The adhesive side of the remaining portion of the sole support strap 10 is pressed onto the mid-sole and heel of the foot with the heel tabs 17 extending beyond the back of the heel (FIG. 7D). The divided heel tabs allow the sole support strap to be used on a wide range of foot sizes. The heel tabs will simply extend further up the back of a smaller foot and extend less on larger feet. If necessary the heel tabs 17 may be cut with a pair of scissors to adjust the length to fit the particular user's foot.

Figure 7E:
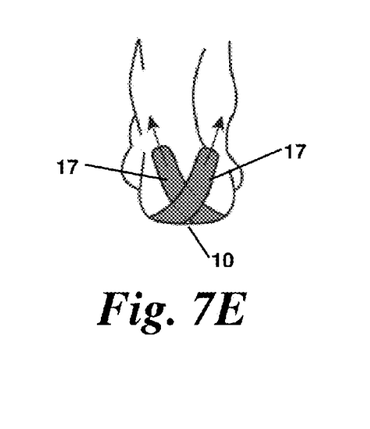

The heel tabs 17 are raised upwardly and pressed onto the back side and lateral sides of the back of the heel in a criss-cross manner over one another (FIG. 7E). The crossed heel tabs form a cradle to support the heel and a sound structure to prevent possible slippage. The crossed heel tabs and cradle route stresses around the center of the heel of the foot to reduce direct pressure on the area of the plantar that is most likely to be injured. The sole support strap 10 is then pressed firmly onto the sole and arch of the foot along its length to ensure adhesion. If necessary, the user may take a step and adjust the position of the sole support strap 10 and/or the heel tabs.

Figure 7F:
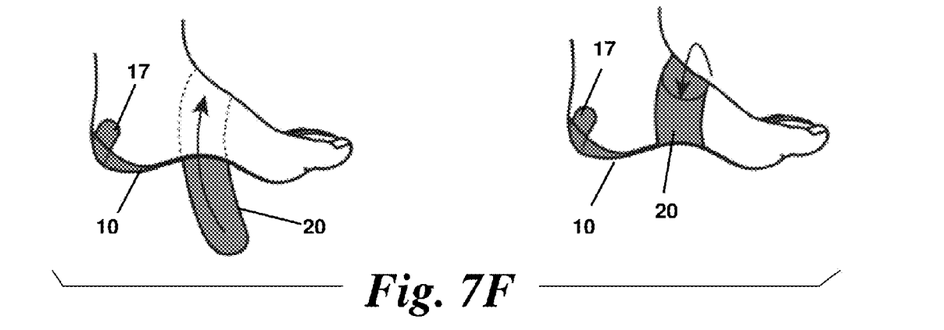
Figure 7G:
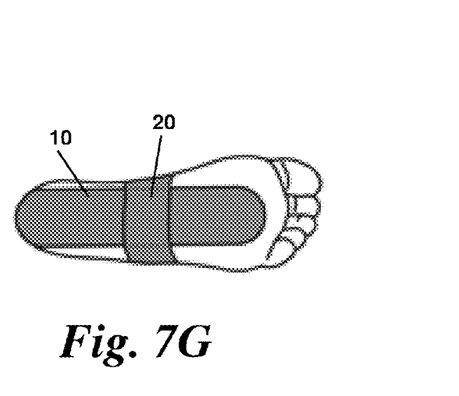
Figure 7H:
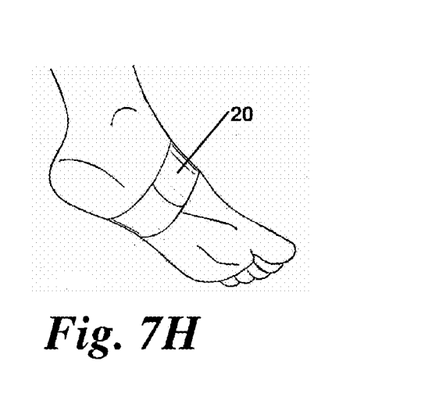

The arch support strap 20 is applied by bending the second longitudinal portion of the release liner backing sheet bearing the arch support strap along the transverse cut so as to expose the facing edges of the first and second shorter segments of the longitudinal release liner backing sheet portion, and peeled off to expose the adhesive side of the arch support strap 20, in the same manner as described above with reference to the sole support strap. As shown in FIGS. 7F and 7G, the mid portion of the arch support strap 20 is placed transversely over the outside of the foot sole support strap member 10 near the middle of the arch and pressed down and the outer sides of the outer ends of the arch support strap are wrapped at least partially over the sides of the arch and pressed down. The outer ends of the arch support strap may or may not overlap on the top of the foot. As discussed above, and as shown in FIG. 7H, the arch support strap 20 when used alone, is adhered transversely under the arch of the foot and at least partially around the outer sides thereof to provide anatomical structural support to the arch, the mid-foot, and the bone structure of the foot, and limit pronation or prevent over pronation.

After the sole support strap 10 and/or the arch support strap 20 has/have been secured to the foot, it/they may be worn all day long even during the load bearing hours of the day, to reduce plantar fascia stress, and thus allow the fascia to rest and recover naturally, and should be removed and discarded on a daily basis. If the user's skin is sensitive or if the product seems difficult to remove, warm water may be applied to aid in removal. Any adhesive residue left on the skin may be removed with warm water and a wash cloth.

A preferred treatment method or regimen for treating arch pain, heel pain, or plantar fasciitis recovery, comprises the following steps: (1) adhesively applying the ultrathin, non-stretch foot support strap system to the foot, as described above, to provide anatomical support to the foot, (2) wearing the foot support strap system during active hours of the day (i.e. anytime while walking or standing), preferably for at least 4-8 hours a day, and most preferably of the bulk of all load bearing hours of the day, which for most individuals is a range averaging 8-24 hours per day, and (3) repeating the process for a period of days; preferably for 3-6 days at a minimum, and most preferably for 6-12 days with all days being consecutive. The used straps should be removed and discarded, and replaced with new supports as required to maintain effectiveness and cleanliness.

Alternatively, the user or medical advisor may monitor heel pain levels and continue to apply and use the foot support strap system for a period of days after a significant decrease in heel pain has occurred, in order to allow any previously damaged fascia time to strengthen. Many users will experience pain reduction within 1-5 days. Lack of pain does not necessarily signify that fascia is completely healed and is strong enough to withstand high impact or high stress activities. The preferred treatment modality, as stated above, is to advise the user to continue to wear the support strap system for a period of days, preferably in a range from 1-6 days after the pain has subsided to allow the fascia to fully recover.

It should be understood that step (1), above, may include use of the arch support strap or sole support strap individually or in combination. The foot support strap system may be packaged to corresponded to the recommended treatment cycle, for example, a package may include a supply of six sole support straps and six arch support straps corresponding to a six day treatment cycle for a single foot.

Referring again to FIG. 2, a sole support strap member 10 and an arch support strap member 20 of the present two-part non-resilient, non-stretch orthotic foot support strap system, illustrated somewhat schematically and with a greater thickness for visibility, are shown attached to the sole of the foot 100. As described previously with reference to FIG. 2, the stress line 300 shows an approximation of the line of forces transferred through the foot 100 during typical motion. The stress line 300 resembles the shape of an archer's bow, and the plantar fascia 110 running along near the bottom surface of the foot 100 is analogous to the string in the archer's bow. Forces that tend to move the ends of the bow apart increase tension on the string. In other words, as forces on the arch push the bones downward, the plantar fascia 110 is subjected to tensile forces.

When adhered to the bottom of the foot, as described previously above, the sole support strap 10 is analogous to another string in the archer's bow connected in parallel with the plantar fascia 110. The sole support strap 10 functions as a tensile load bearing member, in the manner of an external ligament, in the region between the ball of the foot and the heel and, because it substantially inelastic or non-stretchable, it effectively reduces fascia stress through the entire gait cycle, and particularly reduces peak stress in the plantar fascia by maintaining the distance between the ball of the foot and the heel of the foot constant during the heel contact phase, the weight bearing midstance phase, and the propulsion (toe-off or lift-off) propulsion phase of the walking gait cycles; thus, bearing or sharing major tensile loads and stresses, which would otherwise be absorbed primarily by the plantar fascia, and the fascia and surrounding tissues across both the medial and longitudinal arches, to prevent damage to the fascia and allows damaged fascia to heal.

The arch support strap 20, when used in combination with the sole support strap 10, is adhered transversely over the outside of the foot sole support strap member 10, and at least partially over the sides of the arch, and is effective in maintaining the sole support strap 10 in adhesive engagement with the sole of the foot and prevents it from pulling loose in the arch area of the foot, thus assisting the sole support strap member in maintaining proper tension, and also supplements and further aids in supporting the foot and particularly the plantar fascia, and minimizes pronation of the foot (rotation of the medial bones in the midtarsal region of the foot inward and downward). When used alone, the arch support strap 20 is adhered transversely under the arch of the foot and at least partially around the outer sides thereof, and provides anatomical structural support to the arch, the mid-foot, and the bone structure of the foot, and limits pronation or prevents over pronation.

Although the present invention has been shown and described as a disposable two-part non-resilient, non-stretch orthotic foot support strap system that can be adhesively applied to a foot to reduce tensile loads and stresses and provide anatomical support and stability to the musculoskeletal system and the sole, arch, and heel of a foot of a user, and relief from plantar fasciitis, it should be understood, that the present invention may have therapeutic uses to reduce tensile loads and stresses and provide anatomical support and stability to the musculoskeletal system of other parts of the body, where ligament-like support is beneficial.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A disposable, two-part orthotic foot support strap system for treating plantar fasciitis and foot pain by reducing tensile loads and stresses and providing anatomical support to a foot of a user, the system comprising:
   an ultrathin, elongate sole support strap formed of a flexible material having an adhesive layer on an underside surface thereof, said underside surface adapted to be secured to, and extend along, a ball of the foot, a midfoot, and a heel of the user's foot, and conform to a curvature thereof, the sole support strap including a plurality of elongate tabs extending therefrom, wherein a thickness of the sole support strap is less than 1 mm, said flexible material of said sole support strap having a tensile strength of at least 25 lb/in-width in a longitudinal or transverse dimension, and said adhesive layer having a peel strength sufficient to prevent slipping or creeping of said sole support strap when secured to a skin surface of the foot; and
   an ultrathin, elongate arch support strap having an adhesive layer on an underside, the arch support strap adapted to be secured transversely over the sole support strap between the ball and the heel of the user's foot and conform to the curvature thereof, wherein the arch support strap has a ratio of elongate-to-tensile strength that is less than 0.9 in a longitudinal or transverse dimension.

2. The disposable two-part orthotic foot support strap system according to claim 1, further wherein the elongate tabs are configured to be secured to a back side and lateral sides of a back of the user's heel in crossed over relation to one another to form a generally cup-shaped cradle configuration conforming to a contour of the back side of the user's heel to prevent slippage of said sole support strap.

3. The disposable two-part orthotic foot support strap system according to claim 1, wherein a combined thickness of said flexible material and said adhesive layer of said sole support strap is within a range of from about 0.127 mm to about 0.762 mm.

4. The disposable two-part orthotic foot support strap system according to claim 3, wherein the combined thickness of said flexible material and said adhesive layer of said sole support strap is less than 0.381 mm.

5. The disposable two-part orthotic foot support strap system according to claim 1, wherein said sole support strap has an elongation of 0% to 3% in its longitudinal or transverse dimension and said adhesive layer of said sole support strap has a 180° peel strength of at least 15 oz/in as measured in accordance with Pressure Sensitive Tape Council PSTC-3 Standard Adhesion to Steel 180° Peel Test.

6. The disposable two-part orthotic foot support strap system according to claim 1 wherein the arch support strap comprises a preformed, ultrathin elongate generally rectangular strap formed of flexible, non-stretch woven microfiber material; said non-stretch woven microfiber material of said arch support strap having a tensile strength sufficient to prevent stretching and elongation of said sole support strap and said arch support strap in a longitudinal or transverse dimension, and said adhesive layer of the arch support strap having a peel strength sufficient to prevent slipping or creeping of said arch support strap when secured to a skin surface of the foot.

7. The disposable two-part orthotic foot support strap system according to claim 1, wherein a thickness of said arch support strap is less than 1 mm.

8. The disposable two-part orthotic foot support strap system according to claim 1, wherein a thickness of said arch support strap is less than 0.381 mm.

9. The disposable two-part orthotic foot support strap system according to claim 1, wherein said arch support strap has a tensile strength of at least 25 lb/in-width and an elongation of 0% to 3% in its longitudinal or transverse dimension when subjected to applied foot loads and stresses during the phases of a user's walking gait cycle when on the user's foot; and said adhesive layer of said arch support strap has a 180° peel strength of at least 15 oz/in as measured in accordance with Pressure Sensitive Tape Council PSTC-3 Standard Adhesion to Steel 180° Peel Test.

10. The disposable two-part orthotic foot support strap system according to claim 1, wherein said arch support strap has a length and width sufficient to be to secured transversely over said sole support strap, over opposed lateral sides of the midfoot portion of the longitudinal arch, and at least a portion of the instep of the user's foot.

11. A disposable orthotic foot sole support strap for treating plantar fasciitis and foot pain by reducing tensile loads and stresses and providing anatomical support to a foot of a user, the disposable orthotic foot sole support strap comprising:
   an ultrathin, elongate sole support strap formed of a flexible material having an adhesive layer on an underside surface thereof, said underside surface having a contiguous ball of foot portion, a midfoot portion, and a heel portion adapted to be secured to, and extend along, the ball of the foot, the midfoot, and the heel of the user's foot, and conform to the curvature thereof, and a plurality of elongate laterally spaced tabs extending from said sole support strap and configured to be secured to the side of a user's heel in crossed over relation to prevent slippage of said sole support strap, said flexible material having a thickness of less than 1 mm and a tensile strength of at least 25 lb/in-width in at least one direction, and a ratio of elongate-to-tensile strength that is less than 0.9 in a longitudinal or transverse dimension and is sufficient to prevent stretching and elongation of said sole support strap.

12. The disposable orthotic foot sole support strap according to claim 11, wherein said flexible material comprises a layer of a non-stretch woven microfiber material, wherein a thickness of the flexible material and the adhesive layer is between about 0.127 mm to about 0.762 mm.

13. The disposable orthotic foot sole support strap according to claim 11, wherein the thickness of said flexible material and the adhesive layer is less than 0.381 mm.

14. The disposable orthotic foot sole support strap according to claim 11, wherein said flexible material has an elongation of 0% to 3% in its longitudinal or transverse dimension when subjected to applied foot loads and stresses during phases of the user's walking gait cycle.

15. A disposable orthotic foot arch support strap for treating plantar fasciitis and foot pain by reducing tensile loads and stresses and providing anatomical support and stability to a sole, arch and musculoskeletal system of a foot of a user, comprising:

an ultrathin, elongate arch support strap formed of a flexible material having an adhesive layer on an underside surface thereof, said underside surface adapted to be secured transversely over a midfoot portion of a longitudinal arch between the ball of the foot and the heel of the foot and at least a portion of opposed sides of the arch of the user's foot and conform to the curvature thereof, said flexible material having a tensile strength of at least 25 lb/in-width and a ratio of elongate-to-tensile strength that is less than 0.9 in a longitudinal or transverse dimension, and said adhesive layer having a peel strength sufficient to prevent slipping or creeping of said arch support strap when secured to a skin surface of the foot.

16. The disposable orthotic foot arch support strap according to claim 15, wherein a combined thickness of said flexible material and said adhesive layer is less than 1 mm.

17. The disposable orthotic foot arch support strap according to claim 15, wherein a combined thickness of said flexible material and said adhesive layer is less than 1 mm.

18. The disposable orthotic foot arch support strap according to claim 15, wherein said flexible material has an elongation of 0% to 3% in its longitudinal or transverse dimension and said adhesive layer has a 180° peel strength of at least 15 oz/in as measured in accordance with Pressure Sensitive Tape Council PSTC-3 Standard Adhesion to Steel 180° Peel Test.

19. A method for treating plantar fasciitis and foot pain by reducing tensile loads and stresses in a plantar fascia and providing anatomical support and stability to a musculoskeletal system of a foot of a user, comprising the steps of:

removing a release liner sheet from an adhesive layer of an ultrathin, elongate sole support strap formed of a flexible material having the adhesive layer on an underside surface thereof, wherein the adhesive layer is covered by the removable release liner sheet, said underside surface having a contiguous ball of foot portion, a midfoot portion, and a heel portion, said flexible material having a tensile strength of at least 25 lb/in-width and a ratio of elongate-to-tensile strength that is less than 0.9 in a longitudinal or transverse dimension, and said adhesive layer having a peel strength sufficient to prevent slipping or creeping of said sole support strap when secured to a skin surface of the foot; and adhering said ball of foot portion and said midfoot portion of said sole support strap to the skin surface along the ball of the foot and the midfoot to conform to a curvature thereof, and adhering said heel portion to the skin surfaces along the back and lateral sides of the heel of the foot, to conform to a curvature thereof and prevent slippage of said sole support strap, wherein said sole support strap, in the adhered condition, flexes with the foot and provides stability and support to the musculoskeletal system and arch of the user's foot to reduce fascia stress throughout a walking gait cycle.

20. The method according to claim 19, comprising the further steps of:

adhering an arch support strap transversely over the sole support strap, wherein the arch support strap comprises an ultrathin, elongate arch support strap formed of a flexible material having an adhesive layer on an underside surface thereof covered by a removable release liner sheet, said flexible material and said adhesive layer having a peel strength sufficient to prevent slipping or creeping of said arch support strap when secured to a skin surface of the foot;

wherein adhering said arch support strap comprises adhering transversely over said sole support strap and at least a portion of skin surfaces of opposed sides of a midfoot portion of a longitudinal arch between the ball and the heel of the foot to conform to the curvature thereof, such that said arch support strap maintains said sole support strap in adhesive engagement with the sole of the user's foot.

* * * * *